(12) United States Patent
Miyasaka et al.

(10) Patent No.: US 11,710,336 B2
(45) Date of Patent: Jul. 25, 2023

(54) FINGERPRINT DETECTION DEVICE AND DISPLAY DEVICE

(71) Applicant: Japan Display Inc., Tokyo (JP)

(72) Inventors: Koichi Miyasaka, Tokyo (JP); Yoshikatsu Imazeki, Tokyo (JP); Yoichi Kamijo, Tokyo (JP); Shuichi Osawa, Tokyo (JP); Yoshihiro Watanabe, Tokyo (JP)

(73) Assignee: Japan Display Inc., Tokyo (JP)

( * ) Notice: Subject to any disclaimer, the term of this patent is extended or adjusted under 35 U.S.C. 154(b) by 19 days.

(21) Appl. No.: 17/482,709

(22) Filed: Sep. 23, 2021

(65) Prior Publication Data

US 2022/0012450 A1    Jan. 13, 2022

Related U.S. Application Data

(63) Continuation of application No. PCT/JP2020/010370, filed on Mar. 10, 2020.

(30) Foreign Application Priority Data

Mar. 28, 2019    (JP) ................................ 2019-062440

(51) Int. Cl.
*G06K 9/28*    (2006.01)
*G06V 40/13*    (2022.01)
(Continued)

(52) U.S. Cl.
CPC ........ *G06V 40/1306* (2022.01); *G06V 10/147* (2022.01); *G02F 1/13338* (2013.01); *G06F 3/0446* (2019.05)

(58) Field of Classification Search
CPC ............ G06V 40/1306; G06V 40/12–40/1394
See application file for complete search history.

(56) References Cited

U.S. PATENT DOCUMENTS 6,401,551 B1    6/2002 Kawahara et al.
2002/0152048 A1*  10/2002 Hayes ................ G06V 40/1306
                                                          702/127
(Continued)

FOREIGN PATENT DOCUMENTS

JP    H11-110115 A    4/1999
JP    2001-052148 A    2/2001
(Continued)

OTHER PUBLICATIONS

International Search Report issued in International Patent Application No. PCT/JP2020/010370 dated Jun. 9, 2020 and English translation of same. 6 pages.
(Continued)

*Primary Examiner* — Brian Werner
(74) *Attorney, Agent, or Firm* — K&L Gates LLP

(57) ABSTRACT

Provided are a fingerprint detection device and a display device that can reduce the occurrence of unintended patterns. The fingerprint detection device has a plurality of drive electrodes and a plurality of detection electrodes. The detection electrodes have a plurality of first line parts, a plurality of second line parts extending in a direction crossing the first line parts, and bent parts coupling the first line parts and the second line parts to each other. The drive electrodes have a plurality of electrodes arranged spaced apart from each other in a plan view, connecting parts coupling the electrodes adjacent to each other in the second direction to each other, and dummy electrodes in a floating state, each of the dummy electrodes being arranged between two electrodes arranged in the first direction between two detection electrodes.

10 Claims, 12 Drawing Sheets

(51) Int. Cl.
*G06V 10/147* (2022.01)
*G06F 3/044* (2006.01)
*G02F 1/1333* (2006.01)

(56) References Cited

U.S. PATENT DOCUMENTS

2015/0109248 A1 4/2015 Tokai et al.
2015/0370370 A1 12/2015 Ikeda et al.
2017/0372110 A1 12/2017 Uehara et al.

FOREIGN PATENT DOCUMENTS

| JP | 2015-109067 A | 6/2015 |
| JP | 2016-004183 A | 1/2016 |
| JP | 2018-005291 A | 1/2018 |

OTHER PUBLICATIONS

Written Opinion issued in International Patent Application No. PCT/JP2020/010370 dated Jun. 9, 2020. 3 pages.

* cited by examiner

FINGERPRINT DETECTION DEVICE AND DISPLAY DEVICE

CROSS-REFERENCE TO RELATED APPLICATION(S)

This application is a continuation of PCT international application Ser. No. PCT/JP2020/010370 filed on Mar. 10, 2020 which designates the United States, incorporated herein by reference, and which claims the benefit of priority from Japanese Patent Application No. 2019-062440, filed on Mar. 28, 2019, incorporated herein by reference.

BACKGROUND

1. Technical Field

The present invention relates to a fingerprint detection device and a display device.

2. Description of the Related Art

A display device including a liquid crystal panel or the like may be provided with a fingerprint sensor. A fingerprint sensor detects a capacitance change corresponding to a recess or protrusion of a fingerprint to detect the shape of a fingerprint of a finger being in contact with the display device (for example, Japanese Patent Application Laid-open Publication No. 2001-52148). A detection result of the fingerprint sensor is used for personal authentication, for example. The surface of the fingerprint sensor is provided with cover glass. When a finger is in contact with or proximity to the surface of the cover glass, the fingerprint sensor can detect its fingerprint.

Electrodes in a fingerprint detection region reflects light incident from the cover glass side. When the fingerprint detection region is arranged at a position overlapping with a display region of the display device, the electrodes in the fingerprint detection region reflect light, thereby causing a possibility of unintended patterns (e.g., moire and a light reflecting pattern) being visually recognized.

An object of the present invention is to provide a fingerprint detection device and a display device that can reduce the occurrence of unintended patterns.

SUMMARY

A fingerprint detection device according to a first aspect comprising: a substrate; a plurality of drive electrodes provided on one face side of the substrate and arranged in a first direction; and a plurality of zigzag detection electrodes provided on the one face side and arranged in a second direction crossing the first direction, the detection electrodes having: a plurality of first line parts; a plurality of second line parts extending in a direction crossing the first line parts; and bent parts coupling the first line parts and the second line parts to each other, and the drive electrodes having: a plurality of electrodes arranged spaced apart from each other in a plan view; connecting parts coupling the electrodes adjacent to each other in the second direction to each other; and dummy electrodes in a floating state, each of the dummy electrodes being arranged between the two electrodes arranged in the first direction between the two detection electrodes.

A fingerprint detection device according to a second aspect comprising: a substrate; a plurality of drive electrodes provided on one face side of the substrate and arranged in a first direction; and a plurality of zigzag detection electrodes provided on the one face side and arranged in a second direction crossing the first direction, the detection electrodes having: a plurality of first line parts; a plurality of second line parts extending in a direction crossing the first line parts; and bent parts coupling the first line parts and the second line parts to each other, the drive electrodes having a plurality of electrodes having a shape including two parallel sides and arranged spaced apart from each other in a plan view, and a width given by extending a center line between sides of the electrodes facing each other along the sides of the electrodes and causing the center line to reach any of the electrodes and the connecting parts being larger than one time an arrangement spacing of the two bent parts in the second direction and smaller than three times the arrangement spacing.

A display device according to other aspect comprising: a display panel; and the fingerprint detection device according to the first aspect or the second aspect arranged facing the display panel.

DETAILED DESCRIPTION OF THE PREFERRED EMBODIMENTS

The following describes modes (embodiments) for performing the present invention in detail with reference to the accompanying drawings. The details described in the embodiments below do not limit the present invention. Components described below include ones that those skilled in the art can easily assume and substantially the same ones. Further, the components described below can be combined as appropriate. The disclosure is only by way of example, and appropriate changes with the gist of the invention maintained that can be easily thought of by those skilled in the art are naturally included in the scope of the present invention. The drawings may be represented schematically for the width, thickness, shape, and the like of parts compared with actual modes in order to further clarify the description, but they are only by way of example and do not limit the interpretation of the present invention. In the present specification and the drawings, components similar to those described previously as to a drawing discussed previously are denoted by the same symbols, and detailed descriptions thereof may be omitted as appropriate.

First Embodiment

Figure 1:
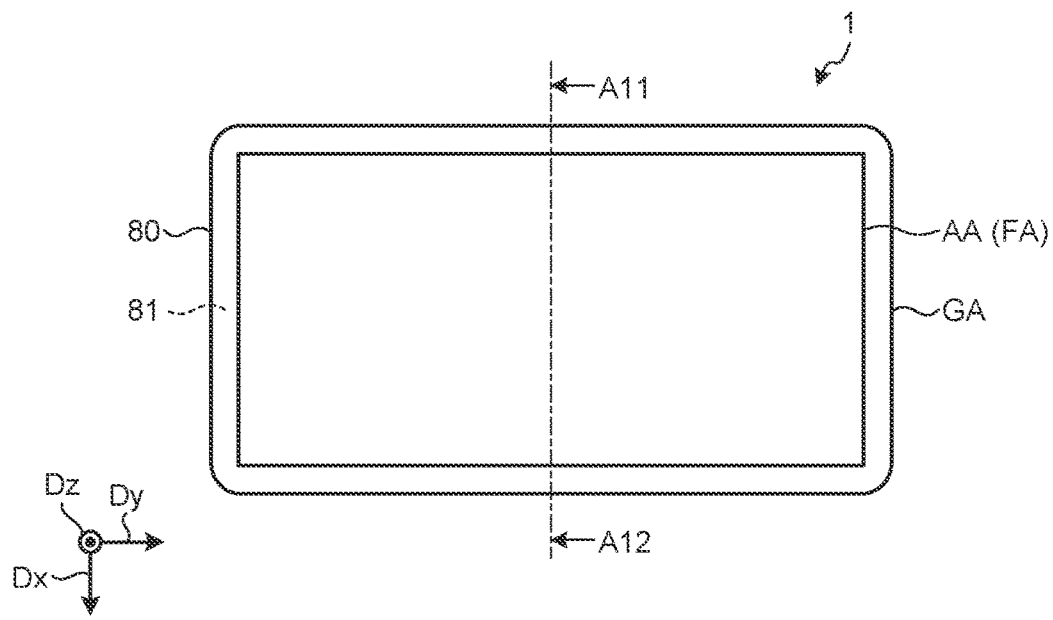
FIG. 1 is a plan view of a display device according to a first embodiment.
Figure 2:
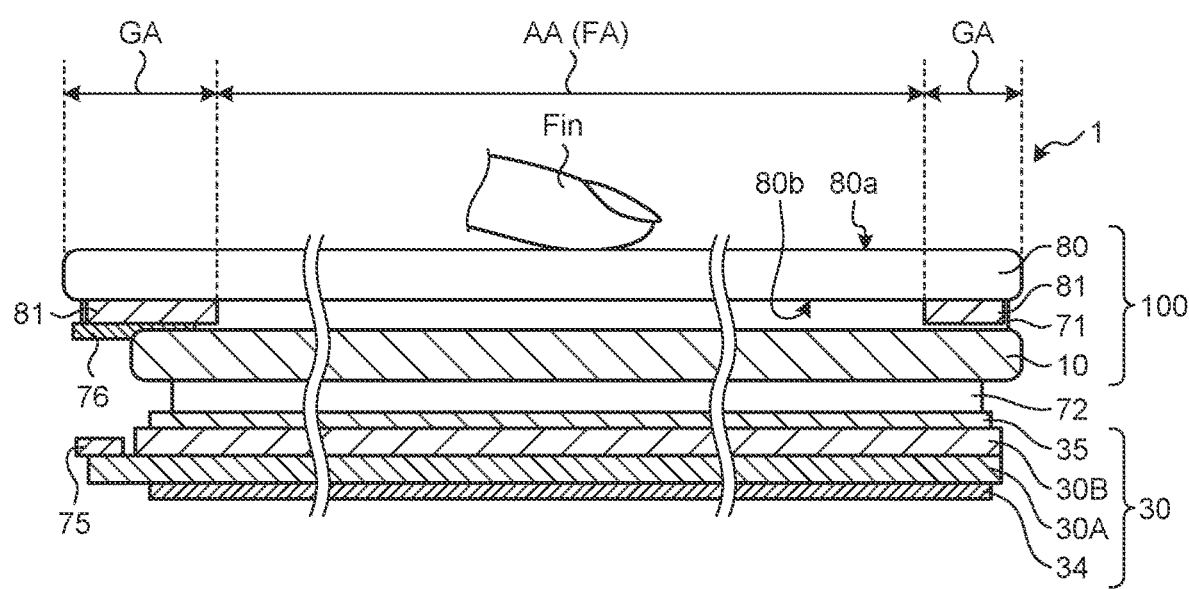
FIG. 2 is a sectional view cutting the display device illustrated in FIG. 1 along the A11-A12 line.

FIG. 1 is a plan view of a display device according to a first embodiment. FIG. 2 is a sectional view cutting the display device illustrated in FIG. 1 along the A11-A12 line. This display device 1 illustrated in FIG. 1 is a display device equipped with a fingerprint detection function and has a display region AA for displaying an image, a fingerprint detection region FA, and a frame region GA provided outside the display region AA and the fingerprint detection region FA. The fingerprint detection region FA is a region for detecting a recess or protrusion on the surface of a finger or the like being in contact with or proximity to a cover member 80. In the display device 1 of the present embodiment, the display region AA and the fingerprint detection region FA match each other or substantially match each other and can detect a fingerprint across the entire face of the display region AA. The shape of the display region AA and the fingerprint detection region FA is rectangular, for example.

As illustrated in FIG. 2, the display device 1 of the present embodiment includes a display panel 30 and a fingerprint detection device 100. The fingerprint detection device 100 has a sensor 10 and the cover member 80. The cover member 80 is a plate-shaped member having a first face 80a and a second face 80b on the side opposite to the first face 80a. The first face 80a of the cover member 80 is a detection face for detecting the recess or protrusion on the surface of the finger or the like being in contact or proximity and is a display face for allowing an observer to visually recognize an image on the display panel 30. The sensor 10 and the display panel 30 are provided on the second face 80b side of the cover member 80. The cover member 80 is a member for protecting the sensor 10 and the display panel 30 and covers the sensor 10 and the display panel 30. The cover member 80 is a glass substrate or a resin substrate, for example.

The cover member 80, the sensor 10, and the display panel 30 are not limited to be rectangular in a plan view and may be circular, oval, or an odd shape with part of these outer shape lacked. The cover member 80 is not limited to be plate-shaped. When the display region AA and the fingerprint detection region FA are curved faces or the frame region GA is a curved face curving toward the display panel 30, for example, the cover member 80 may have a curved face. In this case, the display device is a curved face display having a fingerprint detection function and can detect a fingerprint also on the curved face of the curved face display. "A plan view" indicates a case when viewed in a direction perpendicular to one face 101a of a substrate 101 illustrated in FIG. 3 described below. The direction perpendicular to the one face 101a is "a normal direction Dz of the substrate 101".

As illustrated in FIG. 1 and FIG. 2, in the frame region GA, a decorating layer 81 is provided on the second face 80b of the cover member 80. The decorating layer 81 is a coloring layer lower in the transmittance of light than the cover member 80. The decorating layer 81 can inhibit wiring, circuits, and the like provided superimposed on the frame region GA from being visually recognized by the observer. Although in the example illustrated in FIG. 2 the decorating layer 81 is provided on the second face 80b, it may be provided on the first face 80a. The decorating layer 81 is not limited to a single layer and may be a plurality of laminated layers.

The sensor 10 is a detector for detecting a recess or protrusion on the surface of a finger Fin or the like being in contact with or proximity to the first face 80a of the cover member 80. As illustrated in FIG. 2, the sensor 10 is provided between the cover member 80 and the display panel 30. When viewed in a direction perpendicular to the first face 80a (a normal direction), the sensor 10 overlaps with the fingerprint detection region FA and part of the frame region GA. A flexible substrate 76 is coupled to the sensor 10 in the frame region GA. An IC for detection (not illustrated) for controlling detection operations of the sensor 10 is mounted on the flexible substrate 76.

One face of the sensor 10 is laminated on the second face 80b of the cover member 80 via an adhesive layer 71, whereas the other face thereof is laminated on a polarizing plate 35 of the display panel 30 via an adhesive layer 72. The adhesive layer 71 and the adhesive layer 72 are each an adhesive or a resin having translucency and allows visible light to pass therethrough.

Figure 5:
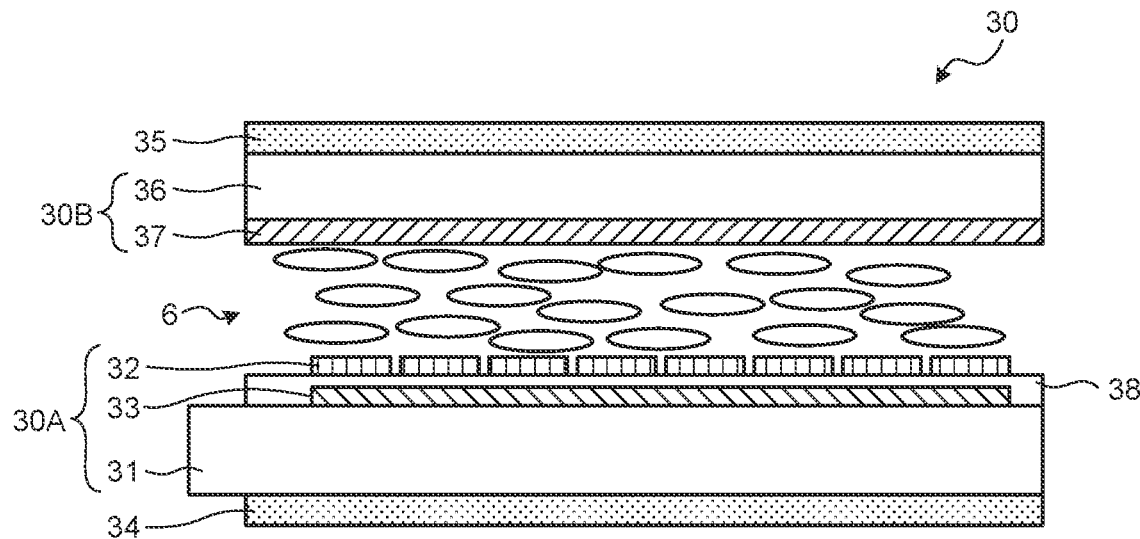
FIG. 5 is a sectional view of a configuration example of a display panel.
Figure 11:
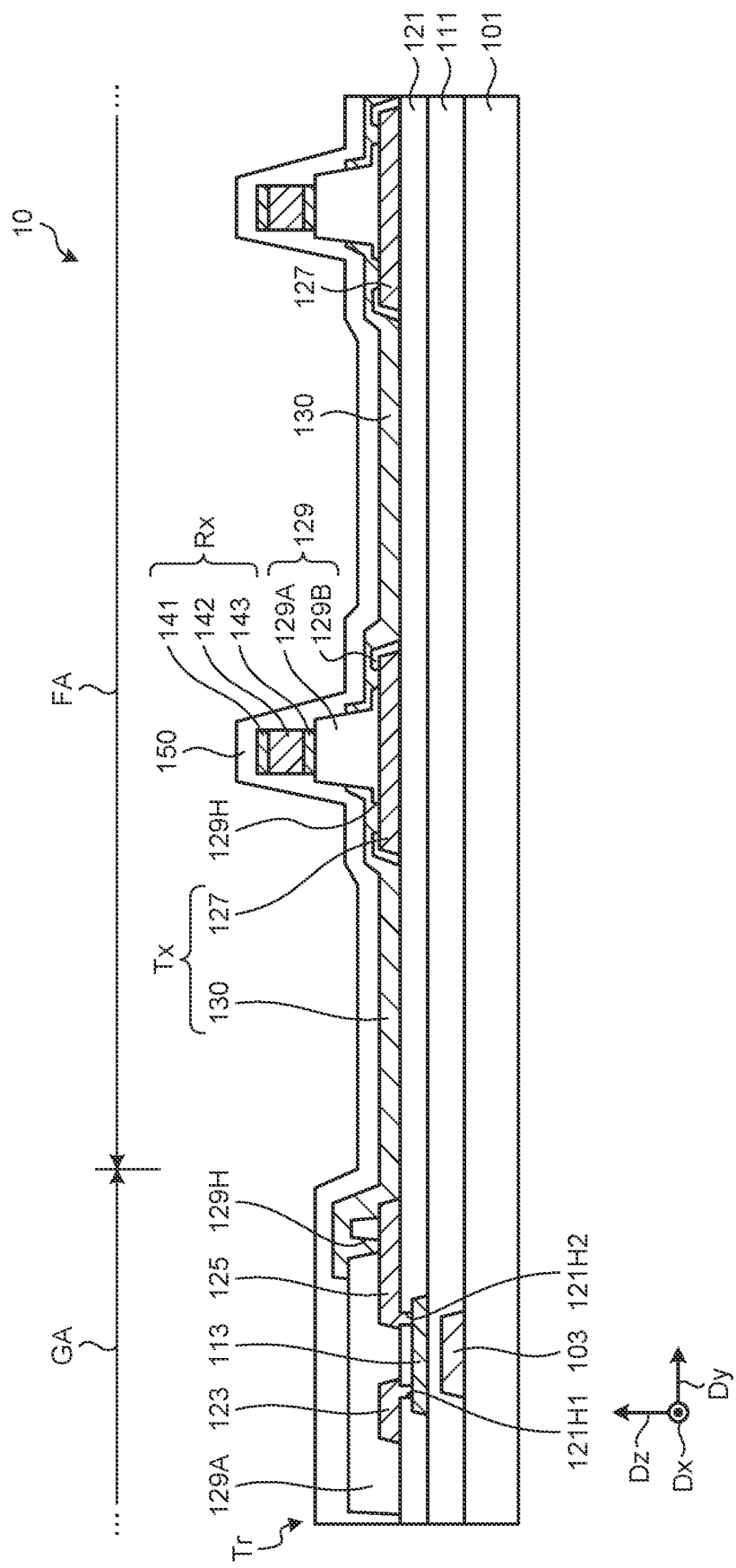
FIG. 11 is a sectional view of a configuration example of the sensor.

The display panel 30 has a pixel substrate 30A, a counter substrate 30B, a polarizing plate 34 provided under the pixel substrate 30A, and the polarizing plate 35 provided over the counter substrate 30B. An IC for display (not illustrated) for controlling a display operation of the display panel 30 is coupled to the pixel substrate 30A via a flexible substrate 75. In the present embodiment, the display panel 30 is a liquid crystal panel in which a liquid crystal element is used as a display function layer; not limited to this example, the display panel 30 may be an organic EL display panel, for example. The IC for detection and the IC for display described above may be provided on a control substrate outside a module. Alternatively, the IC for detection may be provided on the substrate 101 of the sensor 10 (refer to FIG. 3 and FIG. 11). The IC for display may be provided on a first substrate 31 of the pixel substrate 30A (refer to FIG. 5).

Figure 3:
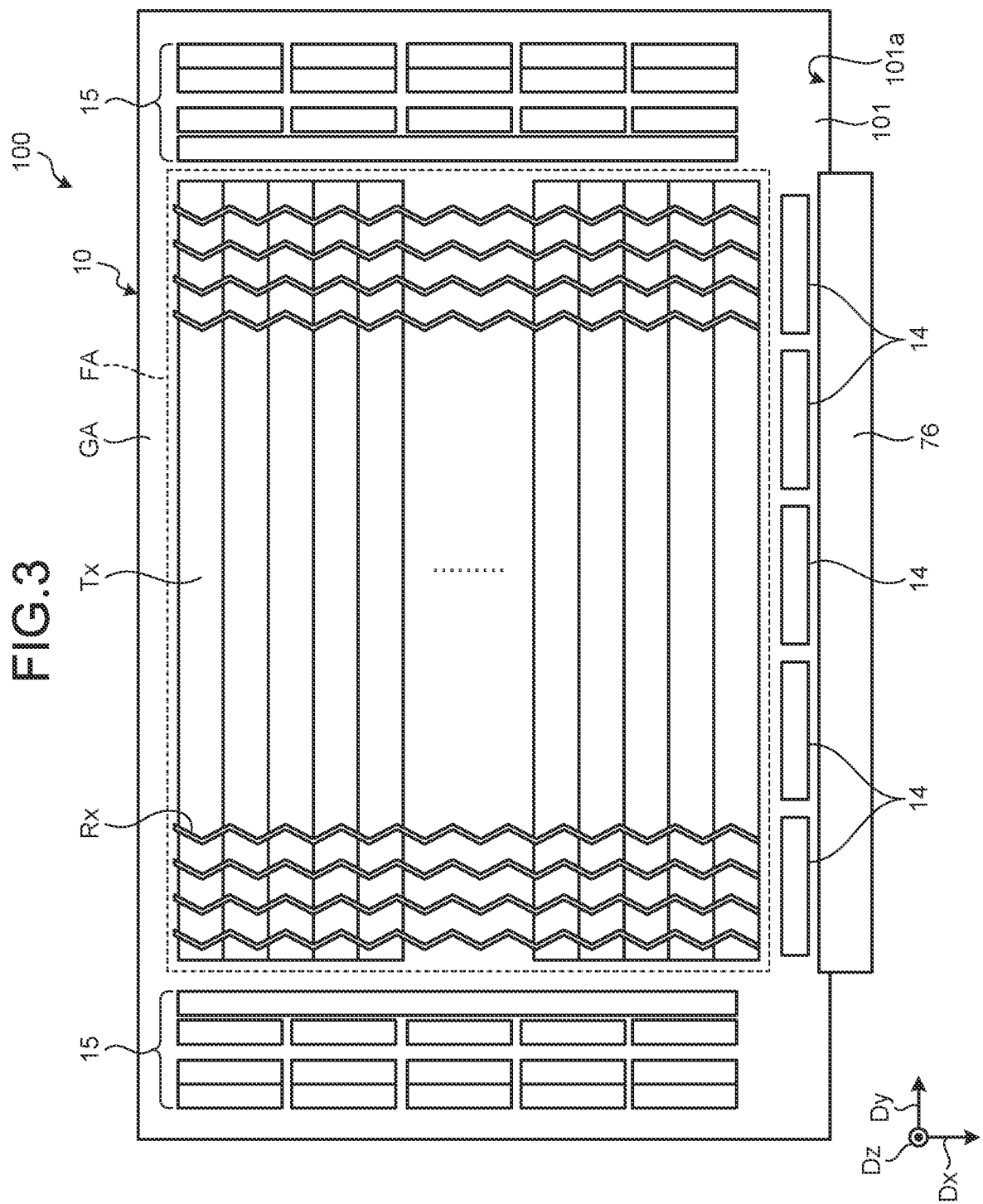
FIG. 3 is a plan view of a configuration example of a fingerprint detection device according to the first embodiment.

FIG. 3 is a plan view of a configuration example of the fingerprint detection device according to the first embodiment. As illustrated in FIG. 3, the fingerprint detection device 100 includes the substrate 101 and the sensor 10 provided on the one face 101a side of the substrate 101. The sensor 10 includes drive electrodes Tx and detection electrodes Rx provided on the one face 101a side of the substrate 101. The substrate 101 is a glass substrate having translucency allowing visible light to pass therethrough. The substrate 101 may be a translucent resin substrate or resin film formed of a resin such as polyimide. The sensor 10 is a sensor having a translucency. The drive electrodes Tx are formed of a translucent conductive material such as indium tin oxide (ITO).

The drive electrodes Tx are arranged in a first direction Dx. The drive electrodes Tx extend in a second direction Dy. The detection electrodes Rx are arranged in the second direction Dy. The detection electrodes Rx extend in the first direction Dx. Thus, the detection electrodes Rx extend in a direction crossing the extension direction of the drive electrodes Tx. The detection electrodes Rx are each coupled to the flexible substrate 75 provided on a short side of the frame region GA of the substrate 101 via frame wiring (not illustrated). In the present embodiment, for the drive electrodes Tx, a conductive material having translucency such as ITO is used. As illustrated in FIG. 3, the drive electrodes Tx and the detection electrodes Rx are provided in the fingerprint detection region FA.

At each of crossing parts between the detection electrodes Rx and the drive electrodes Tx, capacitance is formed. The sensor 10 performs touch detection and fingerprint detection from a capacitance change occurring between the detection electrodes Rx and the drive electrodes Tx. When a mutual capacitance system-based fingerprint detection operation is performed in the sensor 10, a drive electrode driver 15 selects the drive electrodes Tx successively in a time division manner and supplies a drive signal Vs to a selected drive electrode Tx. A detection signal Vdet corresponding to a capacitance change by the recess or protrusion on the surface of the finger or the like being in contact or proximity is output from the detection electrodes Rx, whereby fingerprint detection is performed. The drive electrode driver 15 successively selects each drive electrode block including a plurality of drive electrodes Tx and drives it to perform touch detection.

Although FIG. 3 illustrates a case in which the various kinds of circuits such as a detection electrode selection circuit 14 and the drive electrode driver 15 are provided in the frame region GA of the substrate 101, this is only by way of example. At least part of the various kinds of circuits may be included in the IC for detection mounted on the flexible substrate 76.

Figure 4:
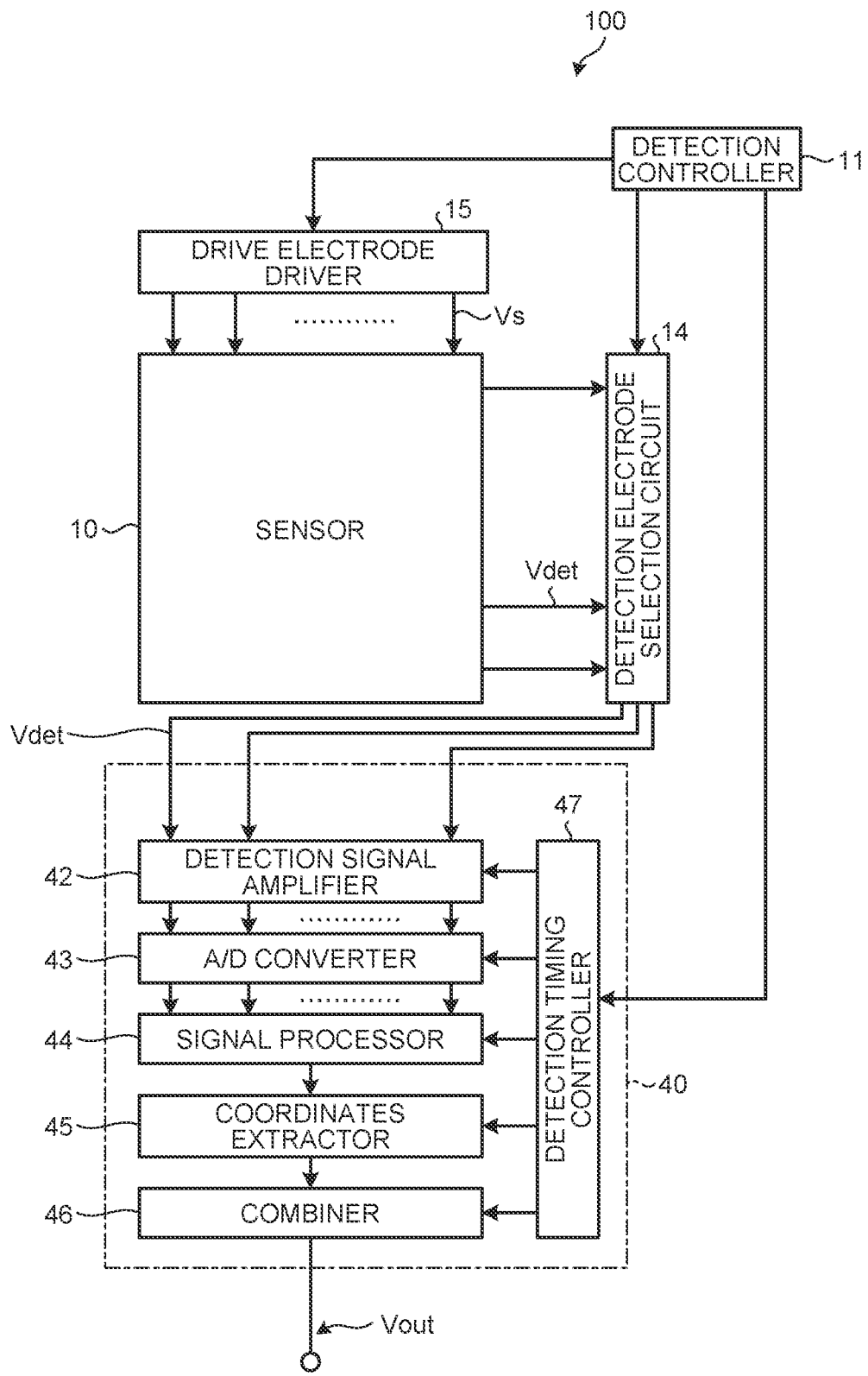
FIG. 4 is a block diagram of a configuration example of the fingerprint detection device.

The following describes a detailed configuration of the fingerprint detection device. FIG. 4 is a block diagram of a configuration example of the fingerprint detection device including the sensor. As illustrated in FIG. 4, the fingerprint detection device 100 includes the sensor 10, a detection controller 11, the drive electrode driver 15, the detection electrode selection circuit 14, and a detector 40.

The detection controller 11 is a circuit controlling detection operations of the sensor 10. The drive electrode driver 15 is a circuit supplying a drive signal Vs for detection to the drive electrodes Tx of the sensor 10 based on a control signal supplied from the detection controller 11. The detection electrode selection circuit 14 selects the detection electrodes Rx of the sensor 10 based on a control signal supplied from the detection controller 11 to couple them to the detector 40.

The detector 40 is a circuit detecting the recess or protrusion on the surface of the finger or the like being in contact with or proximity to the first face 80a of the cover member 80 based on a control signal supplied from the detection controller 11 and the detection signal Vdet output from the detection electrodes Rx to detect the shape of a fingerprint. The detector 40 includes a detection signal amplifier 42, an A/D converter 43, a signal processor 44, a coordinates extractor 45, a combiner 46, and a detection timing controller 47. The detection timing controller 47 performs control to cause the detection signal amplifier 42, the A/D converter 43, the signal processor 44, the coordinates extractor 45, and the combiner 46 to operate in sync with each other based on a control signal supplied from the detection controller 11.

The detection signal Vdet is supplied to the detection signal amplifier 42 of the detector 40 from the sensor 10. The detection signal amplifier 42 amplifies the detection signal Vdet. The A/D converter 43 converts an analog signal output from the detection signal amplifier 42 into a digital signal.

The signal processor 44 is a logic circuit detecting the presence or absence of the contact or proximity of the finger with or to the sensor 10 based on an output signal of the A/D converter 43. The signal processor 44 performs processing to extract a differential signal of a detection signal (an absolute value $|\Delta V|$) by the finger. The signal processor 44 compares the absolute value $|\Delta V|$ with a certain threshold voltage and, if this absolute value $|\Delta V|$ is less than the threshold voltage, determines that the finger is in a noncontact state. In contrast, if the absolute value $|\Delta V|$ is not less than the threshold voltage, the signal processor 44 determines that the finger is in a contact-or-proximity state. Thus, the detector 40 can detect the contact or proximity of the finger.

The coordinates extractor 45 is a logic circuit that, when the contact or proximity of the finger is detected by the signal processor 44, determines its detected coordinates. The coordinates extractor 45 outputs the detected coordinates to the combiner 46. The combiner 46 combines the detection signal Vdet output from the sensor 10 to generate two-dimensional information indicating the shape of the finger being in contact or proximity. The combiner 46 outputs the two-dimensional information as output Vout of the detector 40. Alternatively, the combiner 46 may generate an image based on the two-dimensional information and make image information the output Vout.

The IC for detection described above functions as the detector 40 illustrated in FIG. 4. Part of the functions of the detector 40 may be included in the IC for display described above or be provided as functions of an external microprocessing unit (MPU).

Figure 6:
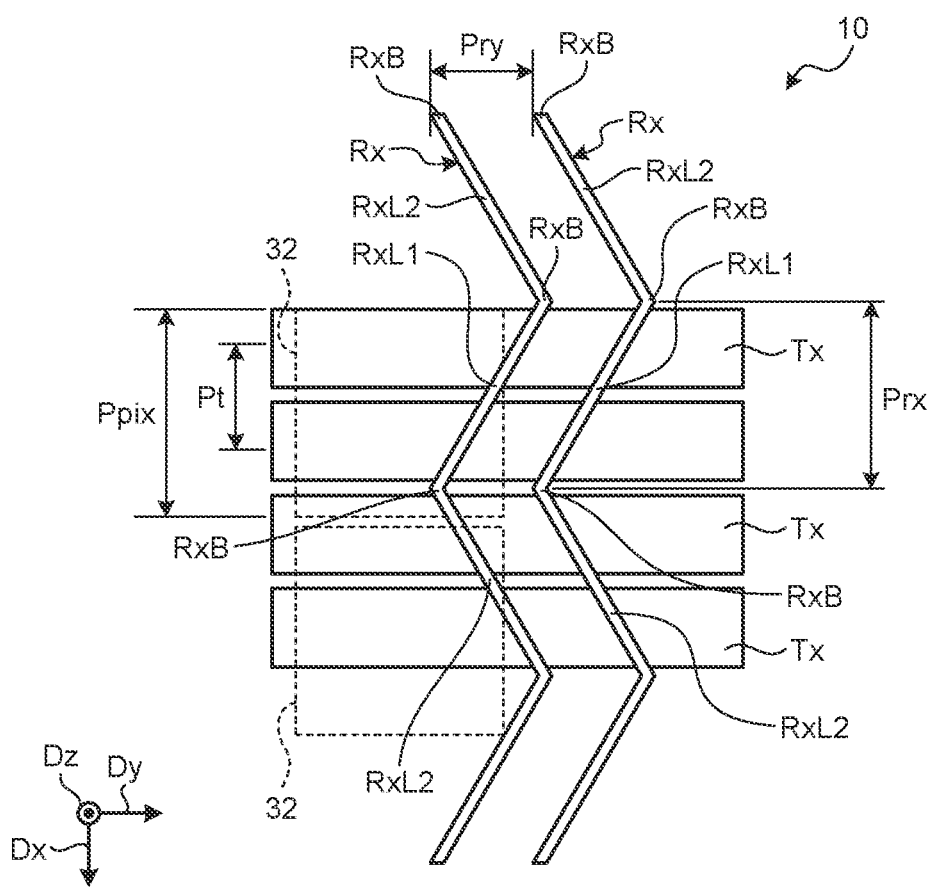
FIG. 6 is a plan view of a configuration example of a sensor according to the first embodiment.

FIG. 6 is a sectional view of a configuration example of a display panel. The pixel substrate 30A includes a first substrate 31, pixel electrodes 32, and a common electrode 33. The common electrode 33 is provided on the first substrate 31. The pixel electrodes 32 are provided above the common electrode 33 via an insulating layer 38 and are arranged in a matrix, or row-column configuration, in a plan view. The pixel electrodes 32 are provided in accordance with subpixels forming each pixel Pix of the display panel 30, and a pixel signal for performing a display operation is supplied thereto. The common electrode 33, to which a DC drive signal for display is supplied, functions as a common electrode for the pixel electrodes 32.

In the present embodiment, the common electrode 33, the insulating layer 38, and the pixel electrodes 32 are stacked in this order relative to the first substrate 31. The polarizing plate 34 is provided under the first substrate 31 via an adhesive layer. Thin film transistors (TFT, not illustrated) as switching elements for display are arranged on the first substrate 31. For the pixel electrodes 32 and the common electrode 33, a conductive material having translucency such as ITO is used, for example.

For the arrangement of the pixel electrodes 32, not only the arrangement in a matrix, or row-column configuration, in which they are arranged in a first direction and a second direction, which is orthogonal to the first direction, adjacent pixel electrodes 32 can be arranged shifted in the first direction or the second direction. Alternatively, based on the difference in size between the adjacent pixel electrodes 32, for one pixel electrode 32 forming a pixel row arranged in the first direction, a plurality of, or two or three, pixel electrodes 32 can be arranged on one side of the pixel electrode.

The counter substrate 30B includes a second substrate 36 and a color filter 37 formed on one face of this second substrate 36. The color filter 37 faces a liquid crystal layer 6 in a direction perpendicular to the first substrate 31. Further, the polarizing plate 35 is provided on the second substrate 36 via an adhesive layer. The color filter 37 may be arranged on the first substrate 31. In the present embodiment, the first substrate 31 and the second substrate 36 are each a glass substrate or a resin substrate, for example.

The liquid crystal layer 6 is provided between the first substrate 31 and the second substrate 36. The liquid crystal layer 6 modulates light passing therethrough in accordance with the state of an electric field; lateral electric field mode liquid crystals such as in-plane switching (IPS) including fringe field switching (FFS) are used, for example. An orientation film may be provided between the liquid crystal layer 6 and the pixel substrate 30A and between the liquid crystal layer 6 and the counter substrate 30B illustrated in FIG. 8.

An illuminator (a backlight, not illustrated) is provided under the first substrate 31. The illuminator has a light source such as a light-emitting diode (LED), for example, and emits light from the light source toward the first substrate 31. The light from the illuminator passes through the pixel substrate 30A, and a part in which the light is shielded not to be emitted and a part in which the light is emitted are switched depending on the state of liquid crystals at that position, whereby an image is displayed on the display face (the first face 80a).

As illustrated in FIG. 2, the display panel 30 is laminated on the sensor 10 via the adhesive layer 72 provided on the polarizing plate 35 in the display region AA. The sensor 10 is arranged at a position closer to the cover member 80 than the display panel 30 in a direction perpendicular to the second face 80b of the cover member 80. The sensor 10 is thus provided closer to the cover member 80, and the distance between the detection electrodes Rx and the first face 80a as the detection face can be reduced compared with a case in which detection electrodes for fingerprint detection are provided integrally with the display panel 30, for example. Consequently, the display device 1 of the present embodiment can improve detection performance.

FIG. 6 is a plan view of a configuration example of detection electrodes of the sensor according to the first embodiment. As illustrated in FIG. 6, the detection electrodes Rx cross the drive electrodes Tx. When viewed in the normal direction Dz, the shape of the detection electrodes Rx is a zigzag line. The detection electrodes Rx extend zigzag in the first direction Dx. The detection electrodes Rx have a plurality of first line parts RxL1, a plurality of second line parts RxL2, and a plurality of bent parts RxB, for example. The second line parts RxL2 extend in a direction crossing the first line parts RxL1. The bent parts RxB couple the first line parts RxL1 and the second line parts RxL2 to each other.

As an example, the first line parts RxL1 extend in a direction crossing the first direction Dx and the second direction Dy. The second line parts RxL2 also extend in a direction crossing the first direction Dx and the second direction Dy. The first line parts RxL1 and the second line parts RxL2 are arranged so as to be bilaterally symmetric about a virtual line (not illustrated) parallel to the first direction Dx.

In each of the detection electrodes Rx, the arrangement spacing of the bent parts RxB in the first direction Dx is defined as Prx. In adjacent detection electrodes Rx, the arrangement spacing of the bent parts RxB in the second direction Dy is defined as Pry. In the present embodiment, Pry<Prx, for example.

The arrangement spacing of the drive electrodes Tx in the first direction Dx is defined as Pt. For the pixel electrodes 32 of the display panel 30 to be laminated on the fingerprint detection device 100, an arrangement spacing in the first direction Dx (the length of the pixel electrodes 32 in the first direction Dx) is defined as Ppix. In the present embodiment, the arrangement spacing Pt of the drive electrodes Tx and the arrangement spacing Ppix of the pixel electrodes 32 preferably satisfy the relation of Expression (1) below. In Expression (1), n is an integer of 1 or more. With this relation, the sensor 10 can reduce the occurrence of unintended patterns (e.g., moire and a light reflecting pattern) in the fingerprint detection region FA.

$$0.6 \times (n-1) \times Ppix \le Pt \le 0.4 \times n \times Ppix \qquad (1)$$

Figure 7:
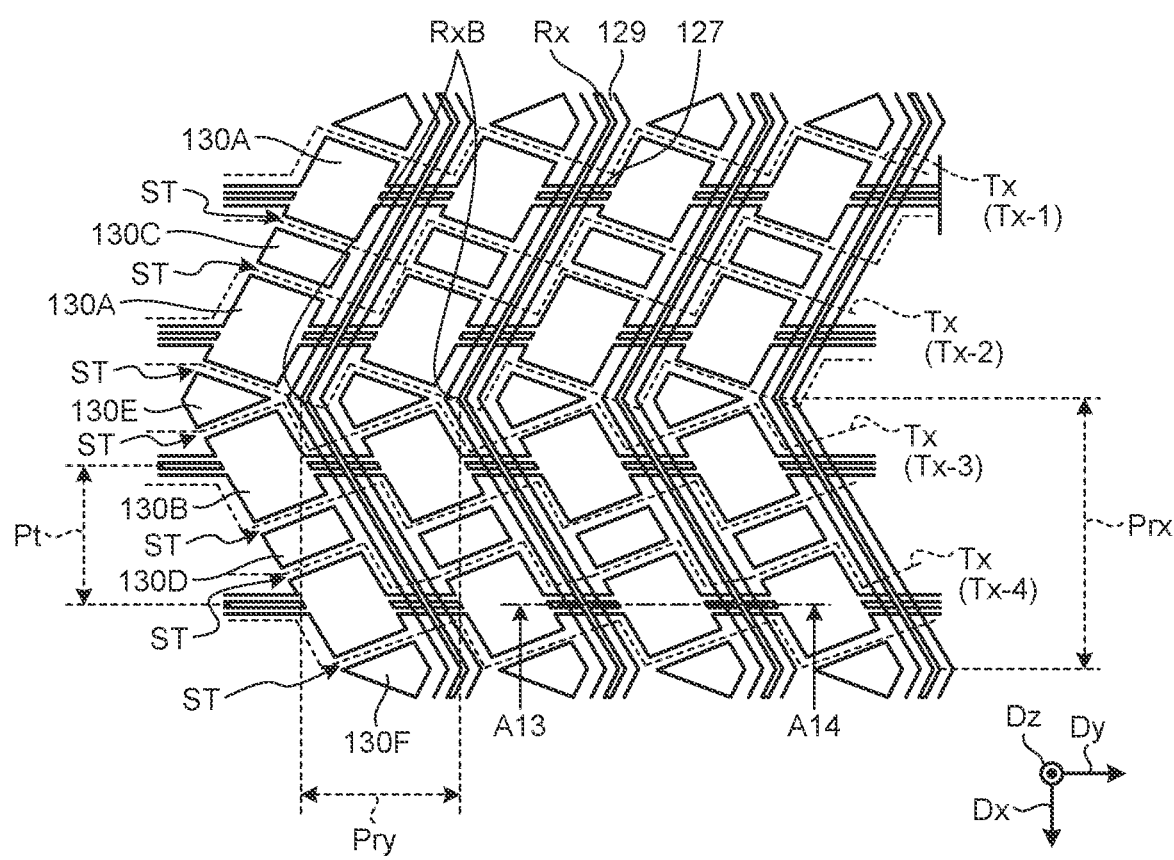
FIG. 7 is a plan view of a configuration example of drive electrodes according to the first embodiment.

The following describes the shape of the drive electrodes Tx more specifically. FIG. 7 is a plan view of a configuration example of the drive electrodes according to the first embodiment. As illustrated in FIG. 7, the drive electrodes Tx (e.g., Tx-1, Tx-2, Tx-3, Tx-4) arranged in the first direction Dx each have a plurality of electrodes 130 and a plurality of connecting parts 127. In each of the drive electrodes Tx, the electrodes 130 are arranged in the second direction Dy and are arranged spaced apart from each other. In each of the drive electrodes Tx, the connecting parts 127 couple adjacent electrodes among the electrodes 130 to each other. As illustrated in FIG. 7, when viewed in the normal direction Dz of the substrate 101 (refer to FIG. 3), one detection electrode Rx crosses the connecting parts 127 through gaps between adjacent electrodes 130.

The longitudinal directions of the connecting parts 127 are aligned in one direction. The connecting parts 127 extend in the second directions. In the first embodiment, an extension line of one connecting part 127 overlaps with another connecting part 127. The longitudinal directions of the connecting parts 127 of one drive electrode Tx are all the second direction, for example. With this alignment, the shape of the connecting parts 127 crossing the detection electrodes Rx is uniform, and the capacitance between the drive electrodes Tx and the connecting parts 127 is easily made uniform.

In the sensor 10 illustrated in FIG. 7, the shape of the drive electrodes Tx, the shape of the detection electrodes Rx, and the positional relation thereof are uniform among the electrodes, and thus variations in the capacitance of the drive electrodes Tx and variations in the capacitance of the detection electrodes Rx are small. In addition, there is an advantage that correction of calculation of coordinates in the sensor 10 is easily executed.

As illustrated in FIG. 7, when viewed in the normal direction Dz, the electrodes 130 have a plurality of shapes. The electrodes 130 include a first electrode 130A and a second electrode 130B the shape of an electrode main body 131 (refer to FIG. 10) of which is different from that of the first electrode 130A, for example. When viewed in the normal direction Dz, the shape of the electrode main body 131 of the first electrode 130A and the shape of the electrode main body 131 of the second electrode 130B are each a parallelogram. When viewed in the normal direction Dz, a shape with the electrode main body 131 of the first electrode 130A vertically inverted is the shape of the electrode main body 131 of the second electrode 130B. With this structure, the area of the electrode main body 131 of the first electrode 130A and the area of the electrode main body 131 of the second electrode 130B are the same.

The drive electrodes Tx-1 and Tx-2 crossing the first line parts RxL1 of the detection electrodes Rx (refer to FIG. 6) include the first electrode 130A having two sides parallel to the first line parts RxL1, for example. The drive electrodes Tx-3 and Tx-4 crossing the second line parts RxL2 of the detection electrodes Rx (refer to FIG. 6) include the second electrode 130B having two sides parallel to the second line parts RxL2. With this structure, when viewed in the normal direction Dz, electrode main bodies 131 can be arranged along the zigzag detection electrode Rx, and a separating distance d3 between the zigzag detection electrode Rx and the electrode main bodies 131 can be a constant length.

There is a dummy electrode 130C between first electrodes 130A arranged in the first direction Dx between two detection electrodes Rx. There is a dummy electrode 130D between second electrodes 130B arranged in the first direction Dx between two detection electrodes Rx. There is a dummy electrode 130E between the first electrode 130A and the second electrode 130B arranged in the first direction Dx between two detection electrodes Rx. There is a dummy electrode 130F between the second electrode 130B and the first electrode 130A arranged in the first direction Dx between two detection electrodes Rx. The dummy electrode refers to an electrode that is not coupled to other conductive parts and is in a floating state, in which the potential is not fixed.

The shape of the dummy electrode 130C and the shape of the dummy electrode 130D are each a parallelogram. The shape of the dummy electrode 130C includes two sides parallel to two sides of the first electrode 130A. The shape of the dummy electrode 130D includes two sides parallel to two sides of the second electrode 130B. When viewed in the normal direction Dz, a shape with the shape of the dummy electrode 130C vertically inverted is the shape of the dummy electrode 130D. With this structure, the area of the dummy electrode 130C and the area of the dummy electrode 130D are the same.

There are a dummy electrode 130E and a dummy electrode 130F between the first electrode 130A and the second electrode 130B arranged in the first direction Dx between two detection electrodes Rx. The shape of the dummy electrode 130E is different from the shapes of the dummy electrode 130C, the dummy electrode 130D, and the dummy electrode 130F. The shape of the dummy electrode 130F is 180-degree rotationally symmetric with the shape of the electrode 130E based on a certain point. Alternatively, it is also said that the dummy electrode 130F has the same shape as that of the dummy electrode 130E and is placed at a position linearly symmetric with the dummy electrode 130F in the first direction Dx. The shape of the dummy electrode 130E and the shape of the dummy electrode 130F each include one side parallel to one side of the first electrode 130A and one side parallel to one side of the second electrode 130B. Dummy electrodes 130E arranged in the second direction Dy are positioned to interpose the bent parts RxB of the detection electrodes Rx therebetween. With this structure, when viewed in the second direction Dy, the dummy electrodes 130E and the bent parts RxB are alternately arranged. Dummy electrodes 130F arranged in the second direction Dy are positioned to interpose the bent parts RxB of the detection electrodes Rx therebetween. With this structure, when viewed in the second direction Dy, the dummy electrodes 130F and the bent parts RxB are alternately arranged. The first electrode 130A, the second electrode 130B, the dummy electrode 130C, and the dummy electrode 130D are formed to be parallelograms, and consequently, conductors of the dummy electrode 130E and the dummy electrode 130F can fill an abnormal shape, which is not a parallelogram, formed between the bent parts RxB arranged in the second direction Dy. The dielectric constant of the part between the bent parts RxB arranged in the second direction Dy can be made comparable to that of the other parts, and thus variations in the capacitance of the drive electrodes Tx by position and variations in the capacitance of the detection electrodes Rx by position can be reduced.

Figure 8:
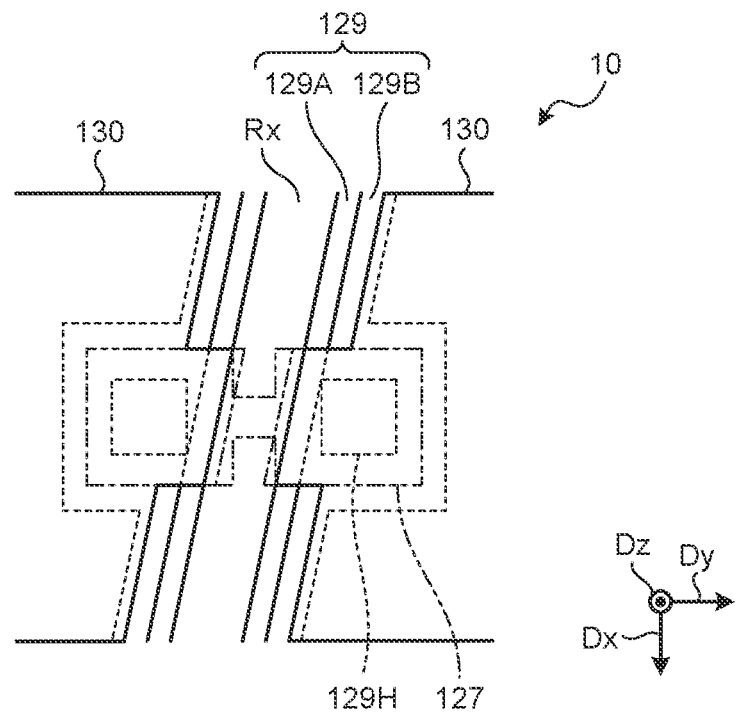
FIG. 8 is a plan view of a drive electrode and a detection electrode according to the first embodiment.
Figure 9:
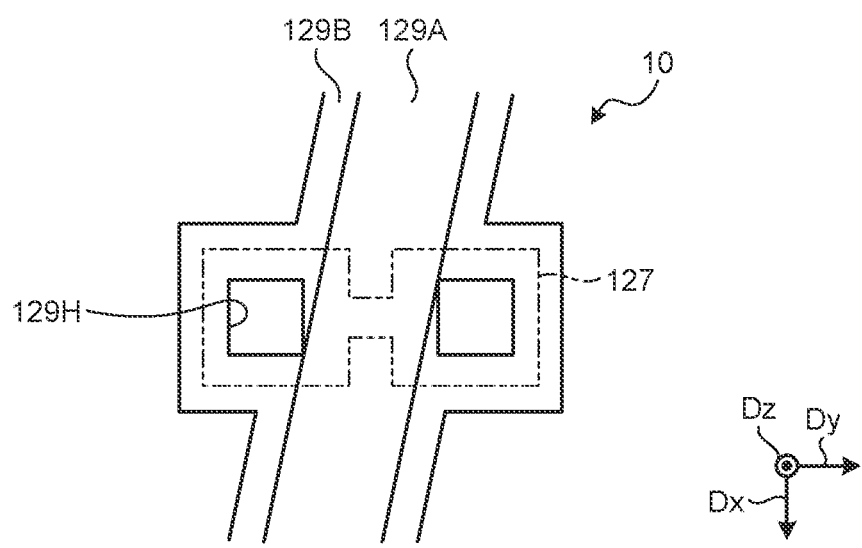
FIG. 9 is a diagram with the illustration of electrodes and the detection electrode omitted in FIG. 8.

FIG. 8 is a plan view of a drive electrode and a detection electrode according to the first embodiment. FIG. 9 is a diagram with the illustration of electrodes and the detection electrode omitted in FIG. 8. As illustrated in FIG. 8, an insulating film 129 is arranged between a connecting part 127 and a detection electrode Rx. The insulating film 129 is a resin insulating film, for example. The insulating film 129 has a first insulating film 129A and a second insulating film 129B thinner than the first insulating film 129A. The second insulating film 129B is provided with a contact hole 129H. As illustrated in FIG. 9, at the bottom of the contact hole 129H, the connecting part 127 is exposed.

Figure 10:
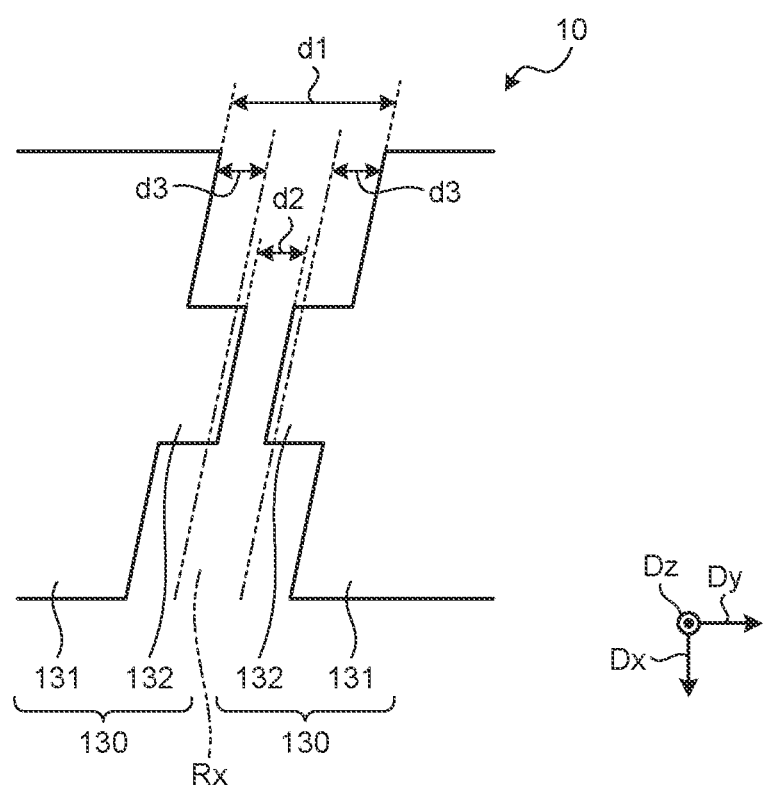
FIG. 10 is a plan view of a configuration example of the electrodes.

FIG. 10 is a plan view of a configuration example of the electrodes. As illustrated in FIG. 10, the electrodes 130 have an electrode main body 131 and a protruding part 132 in a plan view protruding toward an adjacent electrode 130 from the electrode main body 131. The second insulating film 129B is arranged between the protruding part 132 and the connecting part 127. The protruding part 132 embeds the contact hole 129H (refer to FIG. 8) provided in the second insulating film 129B. With this structure, the protruding part 132 is coupled to the connecting part 127 (refer to FIG. 8) via the contact hole 129H. The electrodes 130 are coupled to each other in the second direction Dy via the connecting parts 127.

In the second direction Dy, when the distance between adjacent electrode main bodies 131 is defined as d1, and the distance between adjacent protruding parts 132 is defined as d2, d1>d2. When viewed in the normal direction Dz, the detection electrode Rx is arranged so as to overlap with the protruding parts 132 and capacitance occurring between the electrodes 130 and the detection electrode Rx can be reduced compared with a case in which the electrode main bodies 131 and the detection electrode Rx overlap with each other.

The following describes a layer structure of the sensor. FIG. 9 is a sectional view of a configuration example of the sensor. In FIG. 9, the section of the fingerprint detection region FA is a section cutting the plan view illustrated in FIG. 7 along the A13-A14 line. In FIG. 9, the section of the frame region GA is a section cutting a part including a thin film transistor Tr of the drive electrode driver 15 (refer to FIG. 3). FIG. 9 illustrates the section along the A13-A14 line of the fingerprint detection region FA and the section of the part including the thin film transistor Tr of the frame region GA in a schematically connected manner in order to show a relation between the layer structure of the fingerprint detection region FA and the layer structure of the frame region GA.

Figure 14:
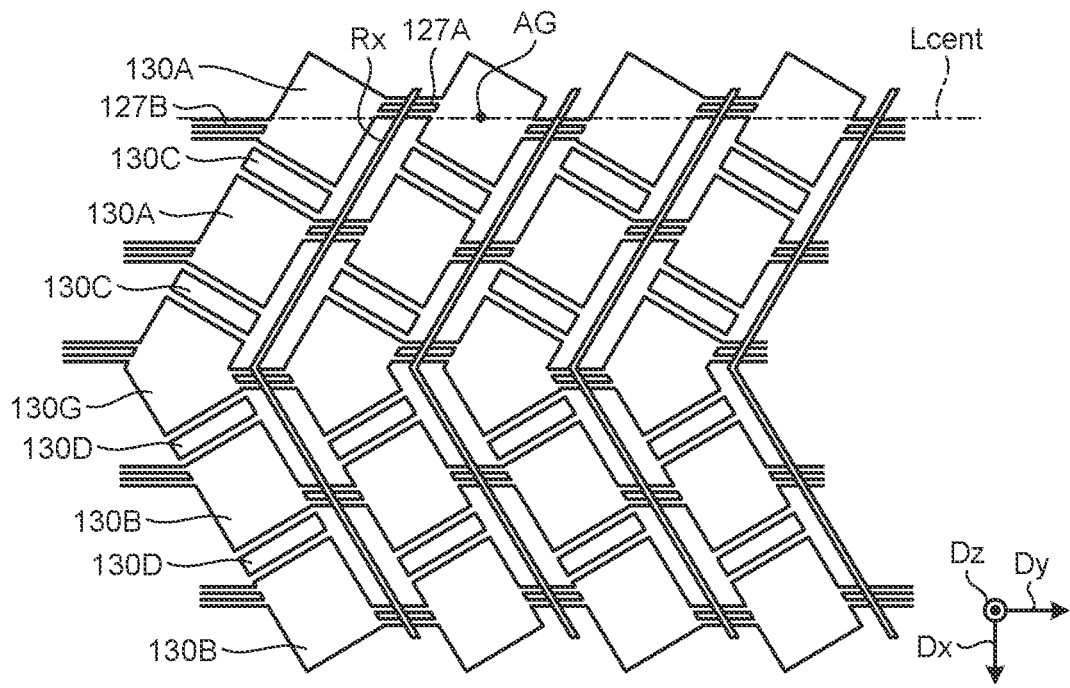
FIG. 14 is a plan view of the sensor according to a second modification of the first embodiment.

As illustrated in FIG. 14, the sensor 10 has the substrate 101, a gate electrode 103 provided on the substrate 101, and a first inter-layer insulating film 111 provided on the substrate 101 to cover the gate electrode 103. The gate electrode 103 is provided in the frame region GA. For the material of the gate electrode 103, aluminum (Al), copper (Cu), silver (Ag), molybdenum (Mo), or an alloy of these is used. For the material of the first inter-layer insulating film 111, a silicon oxide film (SiO), a silicon nitride film (SiN), or a silicon oxide nitride film (SiON) is used. The first inter-layer insulating film 111 is not limited to a single layer and may be a film with a multilayered structure. The first inter-layer insulating film may be a film with a multilayered structure in which a silicon nitride film is formed on a silicon oxide film, for example.

The sensor 10 has a semiconductor layer 113 formed on the first inter-layer insulating film 111 and a second inter-layer insulating film 121 formed on the first inter-layer insulating film 111 to cover the semiconductor layer 113. The second inter-layer insulating film 121 is provided with contact holes 121H1 and 121H2. At the bottom of the contact holes 121H1 and 121H2, the semiconductor layer 113 is exposed. For the material of the semiconductor layer 113, a polysilicon or an oxide semiconductor is used. For the material of the second inter-layer insulating film 121, a silicon oxide film, a silicon nitride film, or a silicon oxide nitride film is used. The second inter-layer insulating film 121 is not limited to a single layer and may be a film with a multilayered structure. The second inter-layer insulating film 121 may be a film with a multilayered structure in which a silicon nitride film is formed on a silicon oxide film, for example.

The sensor 10 has a source electrode 123, a drain electrode 125, and the connecting parts 127 provided on the second inter-layer insulating film 121. The source electrode 123 embeds the contact hole 121H1. The drain electrode 125 embeds the contact hole 121H2. With this structure, the source electrode 123 is coupled to the semiconductor layer 113 via the contact hole 121H1. The drain electrode 125 is coupled to the semiconductor layer 113 via the contact hole 121H2. For the materials of the source electrode 123, the drain electrode 125, and the connecting parts 127, titanium aluminum (TiAl) as an alloy of titanium and aluminum is used.

The gate electrode 103, the semiconductor layer 113, the source electrode 123, and the drain electrode 125 described above are provided in the frame region GA. The gate electrode 103, the semiconductor layer 113, the source electrode 123, and the drain electrode 125 form the thin film transistor Tr in the frame region GA.

The insulating film 129 is provided on the second inter-layer insulating film 121. As described above, the insulating film 129 has the first insulating film 129A and the second insulating film 129B thinner than the first insulating film 129A. The first insulating film 129A provided in the frame region GA covers the source electrode 123 and the drain electrode 125. The first insulating film 129A provided in the frame region GA is provided with the contact hole 129H. The first insulating film 129A provided in the fingerprint detection region FA covers a part positioned under the detection electrode Rx in the connecting part 127. The second insulating film 129B provided in the fingerprint detection region FA covers a part positioned under the electrode 130 in the connecting part 127. As described above, the second insulating film 129B is provided with the contact hole 129H.

Further, the electrodes 130 are provided on the second inter-layer insulating film 121. In the fingerprint detection region FA, the peripheral parts of the electrodes 130 (e.g., the protruding parts 132 illustrated in FIG. 10) embed the contact hole 129H. With this structure, the electrodes 130 are coupled to the connecting parts 127 via the contact hole 129H. In this example, the electrodes 130 are in contact with the second inter-layer insulating film 121.

In the fingerprint detection region FA, the detection electrodes Rx are provided on the first insulating film 129A. The first insulating film 129A insulates the detection electrodes Rx and the drive electrodes Tx from each other. The detection electrodes Rx have a first metallic layer 141, a second metallic layer 142, and a third metallic layer 143, for example. The second metallic layer 142 is provided on the third metallic layer 143, and the first metallic layer 141 is provided on the second metallic layer 142. For the materials of the first metallic layer 141 and the third metallic layer 143, molybdenum or a molybdenum alloy is used, for example. For the material of the second metallic layer 142, aluminum or an aluminum alloy is used. Molybdenum or a molybdenum alloy forming the first metallic layer 141 is lower in the reflectance of visible light than aluminum or an aluminum alloy forming the second metallic layer 142.

An insulating film 150 is provided on the insulating film 129, the electrodes 130, and the detection electrodes Rx. The insulating film 150 covers upper faces and side faces of the detection electrodes Rx. For the insulating film 150, a film with a high refractive index and a low reflectance such as a silicon nitride film is used. Alternatively, the insulating film 150 may be a light-shielding resin film (e.g., a black resin film).

As described above, the sensor 10 according to the first embodiment includes a plurality of drive electrodes Tx provided on the one face 101a side of the substrate 101 and a plurality of detection electrodes Rx provided on the one face 101a side. The drive electrodes Tx are arranged in the first direction Dx. The detection electrodes Rx are arranged in the second direction Dy, which is orthogonal to the first direction Dx. When viewed in the normal direction Dz, the shape of the detection electrodes Rx is a zigzag line. The detection electrodes Rx extend zigzag in the first direction Dx. That is to say, the detection electrodes Rx have a plurality of first line parts RxL1, a plurality of second line parts RxL2, and a plurality of bent parts RxB. The second line parts RxL2 extend in a direction crossing the first line parts RxL1. The bent parts RxB couple the first line parts RxL1 and the second line parts RxL2 to each other.

The drive electrodes Tx have a plurality of electrodes 130 arranged spaced apart from each other and the connecting parts 127 coupling adjacent electrodes among the electrodes 130 to each other. When viewed in the normal direction Dz of the substrate 101, the detection electrodes Rx cross the connecting parts 127 through gaps between the adjacent electrodes 130. With this structure, the electrodes 130 of the drive electrodes Tx can be arranged along the detection electrodes Rx.

The electrodes 130 include the first electrode 130A and the second electrode 130B different in shape from the first electrode 130A when viewed in the normal direction Dz. With this structure, first electrodes 130A can be arranged along the first line parts RxL1, whereas second electrodes 130B can be arranged along the second line parts RxL2. In addition, the separating distance d3 between the electrode main body 131 and the detection electrode Rx can be a constant length. With this structure, the sensor 10 can reduce variations in the capacitance of the detection electrodes Rx caused by the separating distance d3.

The drive electrodes Tx have the dummy electrode 130C in a floating state arranged between two first electrodes 130A arranged in the first direction Dx between two detection electrodes Rx. The drive electrodes Tx have the dummy electrode 130D in a floating state arranged between two second electrodes 130B arranged in the first direction Dx between two detection electrodes Rx. With this structure, the part between the two first electrodes 130A and the part between the two second electrodes 130B are made invisible, and thus the occurrence of unintended patterns can be reduced.

In other words, having the dummy electrode 130C and the dummy electrode 130D makes the distance between the slits ST illustrated in FIG. 7 smaller than the arrangement spacing Pt of the drive electrodes Tx in the first direction Dx, makes the slits ST invisible owing to a relation with the arrangement spacing Ppix of the pixel electrodes 32, and can thus reduce the occurrence of unintended patterns.

The shape of the first electrode 130A in a plan view is a parallelogram. The two first electrodes 130A arranged in the first direction Dx have a shape including two parallel sides, whereas a side of the dummy electrode 130C facing the first electrode 130A is parallel to a side of the first electrode 130A. With this structure, the areas of the two first electrodes 130A are easily made the same. Consequently, the capacitance of the drive electrodes Tx arranged in the first direction Dx is made uniform, thus increasing detection accuracy.

The shape of the second electrode 130B in a plan view is a parallelogram different in shape from the first electrode 130A. The two second electrodes 130B arranged in the first direction Dx have a shape including two parallel sides, whereas a side of the dummy electrode 130D facing the second electrode 130B is parallel to a side of the second electrode 130B. With this structure, the areas of the two second electrodes 130B are easily made the same. Consequently, the capacitance of the drive electrodes Tx arranged in the first direction Dx is made uniform, thus increasing detection accuracy.

Figure 12:
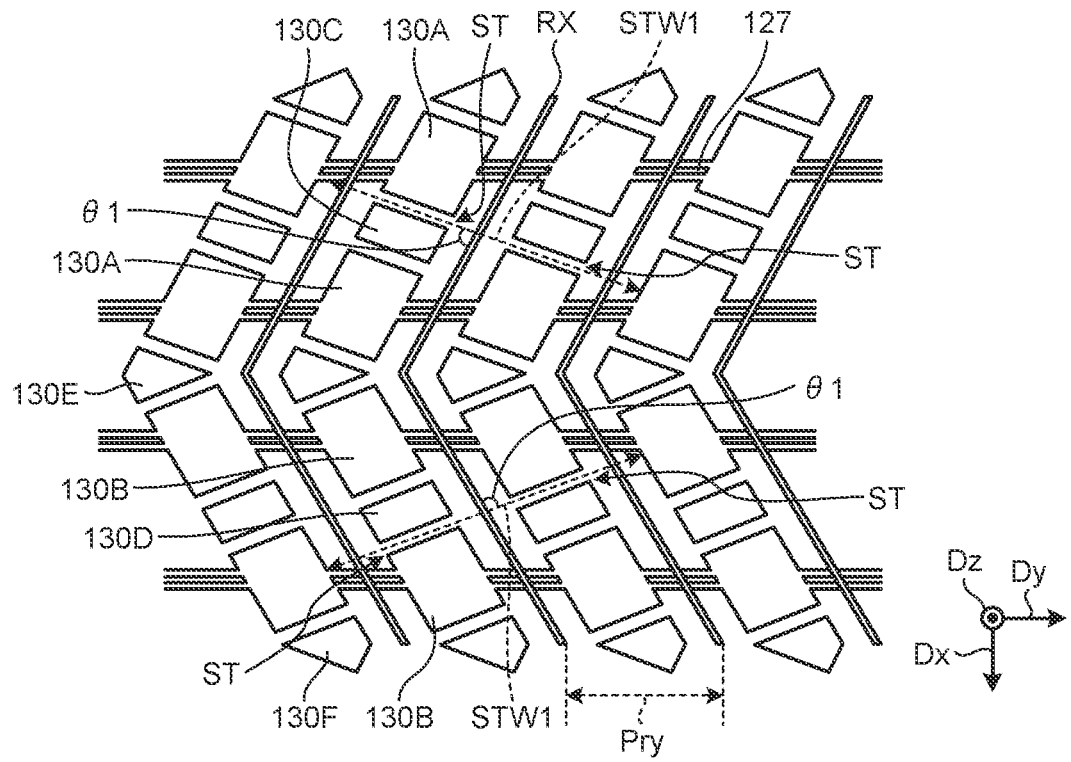
FIG. 12 is a plan view for illustrating slits in FIG. 7.

FIG. 12 is a plan view for illustrating the slits in FIG. 7. As illustrated in FIG. 12, the two slits ST may be continuous across the detection electrode Rx. When three slits ST are continuous across two detection electrodes Rx, there is a possibility that the slits ST will be made visible. Given these circumstances, in the first embodiment, a maximum width STW1 given by extending a center line between a side of the first electrode 130A and a side of the dummy electrode 130C facing the first electrode 130A along the side of the first electrode 130A and causing the center line to reach the first electrodes 130A is larger than one time an arrangement spacing of two bent parts RxB in the second direction Dy and smaller than three times the arrangement spacing. The maximum width STW1 given by extending a center line between a side of the first electrode 130A and a side of the dummy electrode 130C facing the first electrode 130A along the side of the first electrode 130A and causing the center line to reach the first electrodes 130A is larger than one time an arrangement spacing of two bent parts RxB in the second direction Dy and smaller than three times the arrangement spacing. In other words, the three slits ST are not continuous across two detection electrodes Rx. With this structure, the slits ST are made invisible, and the occurrence of unintended patterns can be reduced.

When the center line between the side of the first electrode 130A and the side of the dummy electrode 130C facing the first electrode 130A is extended along the side of the first electrode 130A, and the center line reaches the dummy electrode 130C, the width between dummy electrodes 130C that the center line reaches may be the maximum width STW1.

When the center line between the side of the first electrode 130A and the side of the dummy electrode 130C facing the first electrode 130A is extended along the side of the first electrode 130A, and a first angle θ1 formed by the center line and the detection electrode Rx is 90 degrees, the occurrence of unintended patterns such as moire can be reduced. Thus, the first angle θ1 is preferably 90 degrees. Similarly, the center line between the side of the second electrode 130B and the side of the dummy electrode 130D facing the second electrode 130B is extended along the side of the second electrode 130B, and the first angle θ1 given by the center line and the detection electrode Rx, is also preferably 90 degrees.

The sensor 10 further includes the first insulating film 129A arranged between the connecting part 127 and the detection electrode Rx and the second insulating film 129B arranged between the connecting part 127 and the electrode 130. The second insulating film 129B is thinner than the first insulating film 129A. With this structure, the sensor 10 can reduce a step of the electrode 130 compared with a case in which the electrode 130 is arranged on the first insulating film 129A. With this structure, the sensor 10 can reduce the possibility of a break occurring in the electrode 130. The first insulating film 129A arranged between the connecting part 127 and the detection electrode Rx is larger in thickness than the second insulating film 129B and can thus reduce the capacitance of the detection electrodes Rx.

The electrodes 130 are translucent electrodes, whereas the detection electrodes Rx are metallic thin lines. With this structure, the detection electrodes Rx can be reduced in resistance and reduced in capacitance. The detection electrodes Rx are metallic thin lines and are thus small in electrode width. With this structure, the area covered with the detection electrodes Rx can be reduced. Consequently, the sensor 10 can make the aperture of the fingerprint detection region FA higher and can increase the translucency of the fingerprint detection region FA.

In the first direction Dx, the ratio of the arrangement spacing Prx of the bent parts RxB to the arrangement spacing Pt of the drive electrodes Tx is preferably 2 or less. With this structure, the sensor 10 can reduce the occurrence of unintended patterns such as moire.

First Modification

Figure 13:
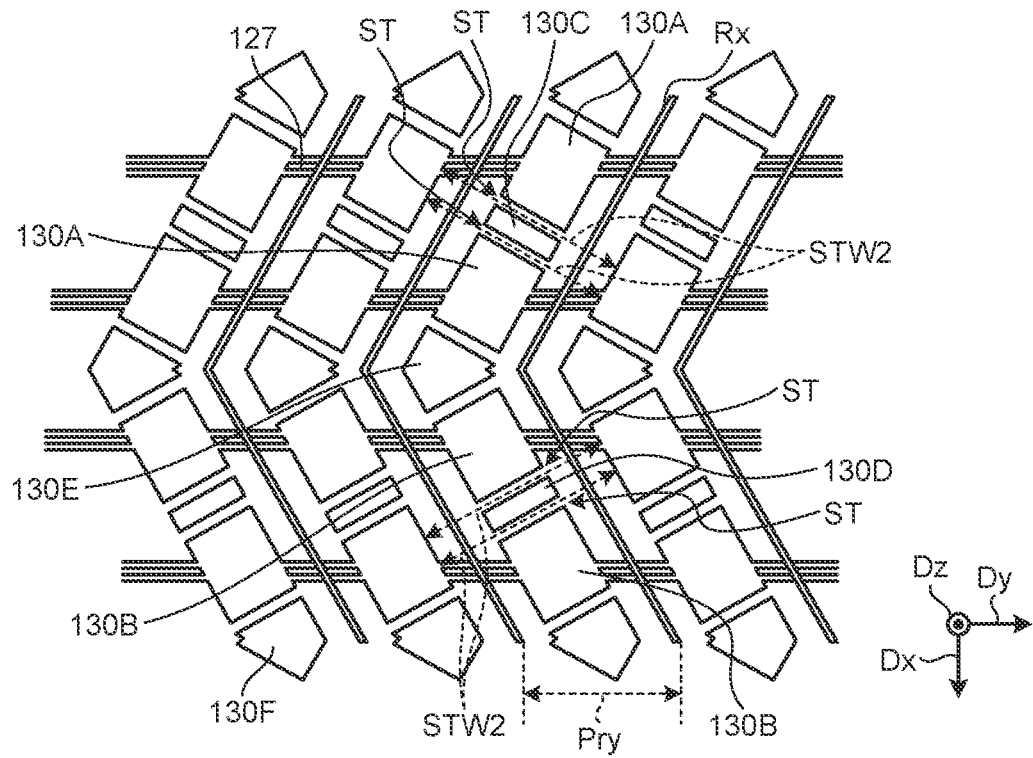
FIG. 13 is a plan view of the sensor according to a first modification of the first embodiment.

FIG. 13 is a plan view of the sensor according to a first modification of the first embodiment. The same components as those described in the first modification described above are denoted by the same symbols, and a duplicate description is omitted. As illustrated in FIG. 13, two slots ST are not continuous across the detection electrode Rx.

In the first modification of the first embodiment, a maximum width STW2 given by extending a center line between a side of the first electrode 130A and a side of the dummy electrode 130C facing the first electrode 130A along the side of the first electrode 130A and causing the center line to reach the first electrodes 130A is larger than one time an arrangement spacing of two bent parts RxB in the second direction Dy and smaller than double the arrangement spacing. The maximum width STW2 given by extending a center line between a side of the second electrode 130B and a side of the dummy electrode 130D facing the second electrode 130B along the side of the second electrode 130B and causing the center line to reach the second electrodes 130B is larger than one time an arrangement spacing Pry of two bent parts in the second direction Dy and smaller than double the arrangement spacing. With this structure, the slits ST are made invisible, and the occurrence of unintended patterns can be reduced.

Second Modification

FIG. 14 is a plan view of the sensor according to a second modification of the first embodiment. The same components as those described in the first modification described above are denoted by the same symbols, and a duplicate description is omitted. Although a connecting part 127A and a connecting part 127B have the same multilayered structure as that of the connecting parts 127 described above, they are different therefrom in connecting positions with the electrodes 130 in a plan view.

In each of the drive electrodes Tx, the connecting part 127A and the connecting part 127B are preferably alternately arranged on one side and the other side of a virtual line Lcent parallel to the second direction Dy and passing through an areal gravity center AG of the electrodes 130. With this structure, the connecting parts 127, which are lower in the transmittance of light than the electrodes 130, are not arranged on a straight line, and the sensor 10 can thus reduce the occurrence of unintended patterns such as moire.

Second Embodiment

Figure 15:
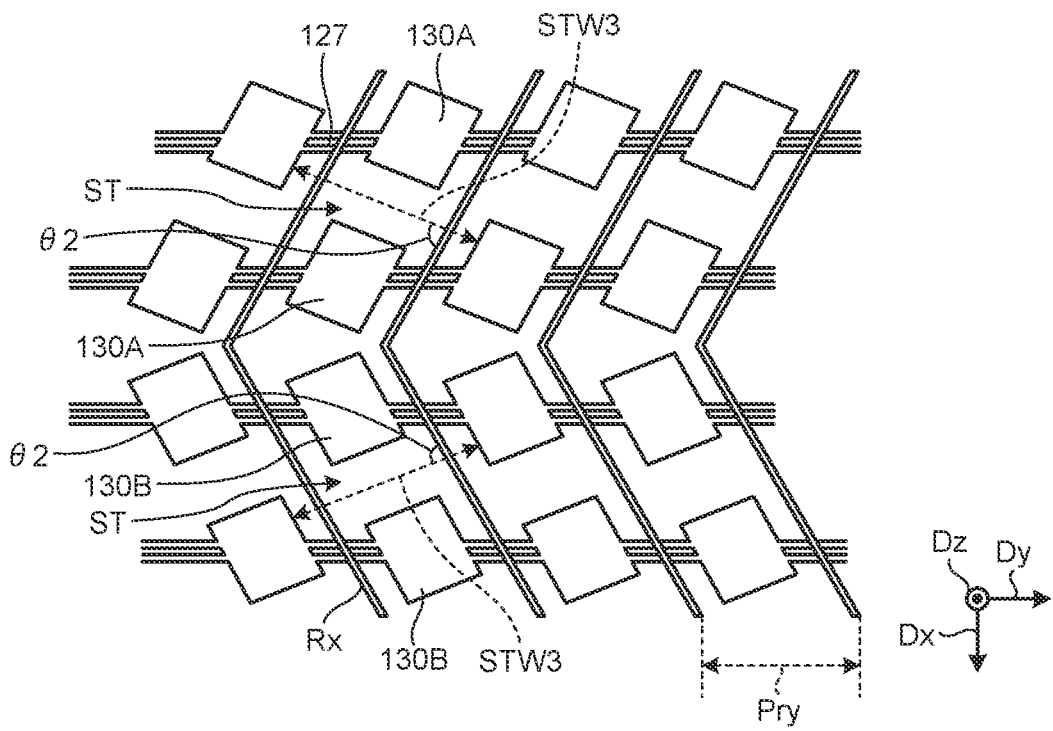
FIG. 15 is a plan view of the sensor according to a second embodiment.

FIG. 15 is a plan view of the sensor according to a second embodiment. The same components as those described in the first embodiment described above are denoted by the same symbols, and a duplicate description is omitted. The embodiment does not include the dummy electrode 130C, the dummy electrode 130D, the dummy electrode 130E, and the dummy electrode 130F, which are included in the first embodiment.

As illustrated in FIG. 15, a width STW3 given by extending a center line between sides of the first electrodes 130A facing each other along the sides of the first electrodes 130A and causing the center line to reach the first electrodes 130A is larger than one time the arrangement spacing Pry of two bent parts in the second direction Dy and smaller than double the arrangement spacing. The width STW3 given by extending a center line between sides of the second electrodes 130B facing each other along the sides of the second electrodes 130B and causing the center line to reach the second electrodes 130B is larger than one time the arrangement spacing Pry of two bent parts in the second direction Dy and smaller than double the arrangement spacing. In other words, the two slits ST are not continuous across one detection electrode Rx. With this structure, the sensor 10 can reduce the occurrence of unintended patterns such as moire.

When the center line between the sides of the first electrodes 130A facing each other is extended along the sides of the first electrodes 130A, and a second angle θ2 formed by the center line and the detection electrode Rx is 90 degrees, the occurrence of unintended patterns such as moire can be reduced. Thus, the second angle θ2 is preferably 90 degrees. The center line between the sides of the second electrodes 130B facing each other is extended along the sides of the second electrodes 130B, and the second angle θ2 formed by the center line and the detection electrode Rx is also preferably 90 degrees.

As illustrated in FIG. 15, even if the slit SW is a maximum width connected across the detection electrodes Rx, it is larger than one time the arrangement spacing Pry of two bent parts in the second direction Dy and smaller than three times the arrangement spacing. With this structure, the sensor 10 can reduce the occurrence of unintended patterns such as moire.

First Modification of Second Embodiment

Figure 16:
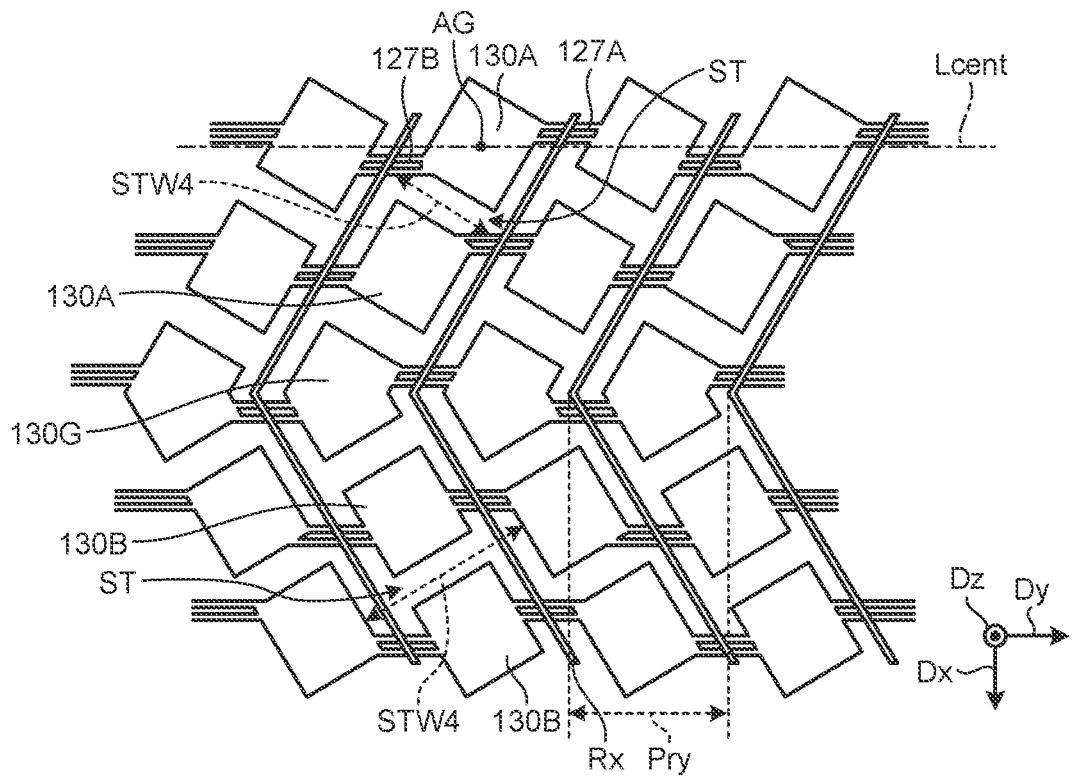
FIG. 16 is a plan view of the sensor according to a first modification of the second embodiment.

FIG. 16 is a plan view of the sensor according to a first modification of the second embodiment. The same components as those described in the first modification described above are denoted by the same symbols, and a duplicate description is omitted. The embodiment does not include the dummy electrode 130C, the dummy electrode 130D, the dummy electrode 130E, and the dummy electrode 130F, which are included in the first embodiment.

In each of the drive electrodes Tx, the connecting part 127A and the connecting part 127B are preferably alternately arranged on one side and the other side of the virtual line Lcent parallel to the second direction Dy and passing through the areal gravity center AG of the electrodes 130. With this structure, the connecting parts 127, which are lower in the transmittance of light than the electrodes 130, are not arranged on a straight line, and the sensor 10 can thus reduce the occurrence of unintended patterns such as moire.

As illustrated in FIG. 16, a width STW4 given by extending a center line between sides of the first electrodes 130A facing each other along the sides of the first electrodes 130A and causing the center line to reach the connecting part 127A or the connecting part 127B is larger than one time the arrangement spacing Pry of two bent parts in the second direction Dy and smaller than double the arrangement spacing. The width STW4 given by extending a center line between sides of the second electrodes 130B facing each other along the sides of the second electrodes 130B and causing the center line to reach the connecting part 127A or the connecting part 127B is larger than one time the arrangement spacing Pry of two bent parts in the second direction Dy and smaller than double the arrangement spacing. With this structure, the sensor 10 can reduce the occurrence of unintended patterns such as moire.

The shape of a third electrode 130G is different from the shape of the first electrode 130A and the second electrode 130B. The shape of the third electrode 130G includes one side parallel to one side of the first electrode 130A and one side parallel to one side of the second electrode 130B. Third electrodes 130G arranged in the second direction Dy are positioned to interpose the bent parts RxB of the detection electrodes Rx therebetween. With this structure, when viewed in the second direction Dy, the third electrodes 130G and the bent parts RxB are alternately arranged. The first electrode 130A and the second electrode 130B are formed to be parallelograms, and consequently, a conductor of the third electrode 130G can fill an abnormal shape, which is not a parallelogram, formed between the bent parts RxB arranged in the second direction Dy.

Second Modification of Second Embodiment

Figure 17:
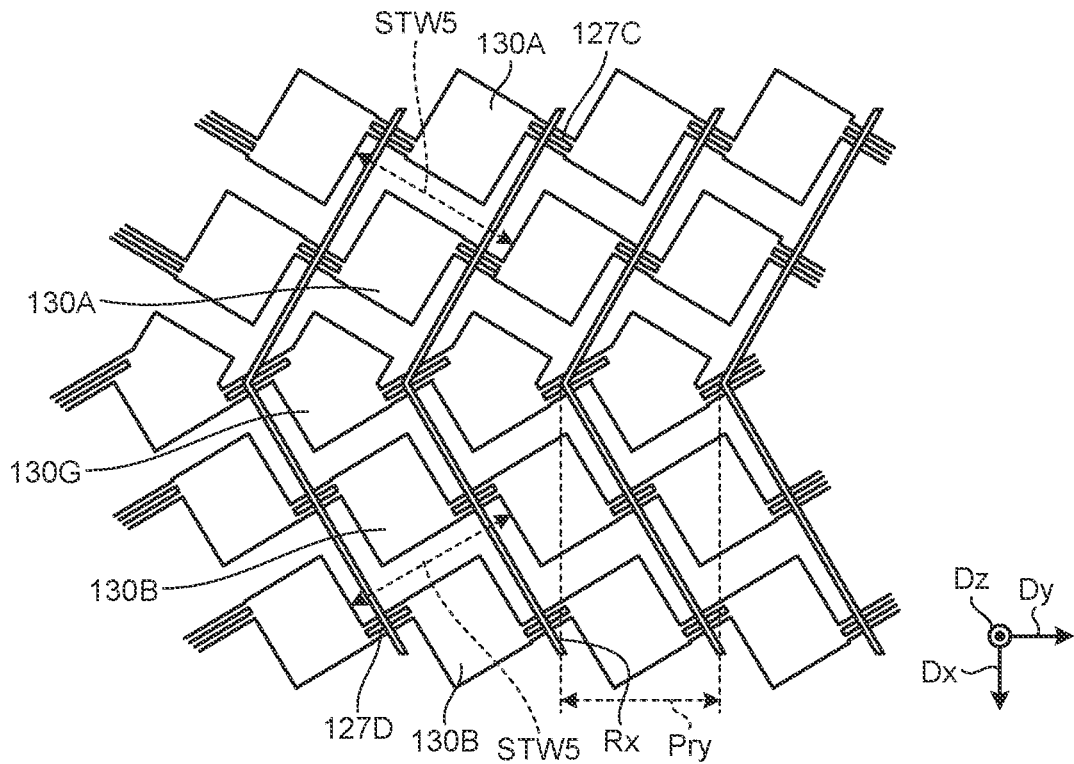
FIG. 17 is a plan view of the sensor according to a second modification of the second embodiment.

FIG. 17 is a plan view of the sensor according to a second modification of the second embodiment. The same components as those described in the first embodiment, the second embodiment, and the modifications thereof described above are denoted by the same symbols, and a duplicate description is omitted. The embodiment does not include the dummy electrode 130C, the dummy electrode 130D, the dummy electrode 130E, and the dummy electrode 130F, which are included in the first embodiment. Although a connecting part 127C and a connecting part 127D have the same multilayered structure as that of the connecting parts 127 described above, they are different therefrom in connecting positions with the electrodes 130 and directions in which they extend in a plan view.

In each of the drive electrodes Tx, the connecting part 127C extends in a direction along a side of the first electrode 130A. The connecting part 127D extends in a direction along a side of the second electrode 130B. The direction in which the connecting part 127C extends and the direction in which the connecting part 127D extends are different from each other. Neither the direction in which the connecting part 127C extends nor the direction in which the connecting part 127D extends are parallel to the first direction Dx and the second direction Dy. With this structure, the connecting parts 127, which are lower in the transmittance of light than the electrodes 130, are not arranged on a straight line in the first direction Dx and the second direction Dy, and the sensor 10 can thus reduce the occurrence of unintended patterns such as moire.

As illustrated in FIG. 17, a width STW5 given by extending a center line between sides of the first electrodes 130A facing each other along the sides of the first electrodes 130A and causing the center line to reach the first electrodes 130A is larger than one time the arrangement spacing Pry of two bent parts in the second direction Dy and smaller than double the arrangement spacing. The width STW5 given by extending a center line between sides of the second electrodes 130B facing each other along the sides of the second electrodes 130B and causing the center line to reach the second electrodes 130B is larger than one time the arrangement spacing Pry of two bent parts in the second direction Dy and smaller than double the arrangement spacing. With this structure, the sensor 10 can reduce the occurrence of unintended patterns such as moire.

Third Embodiment

Figure 18:
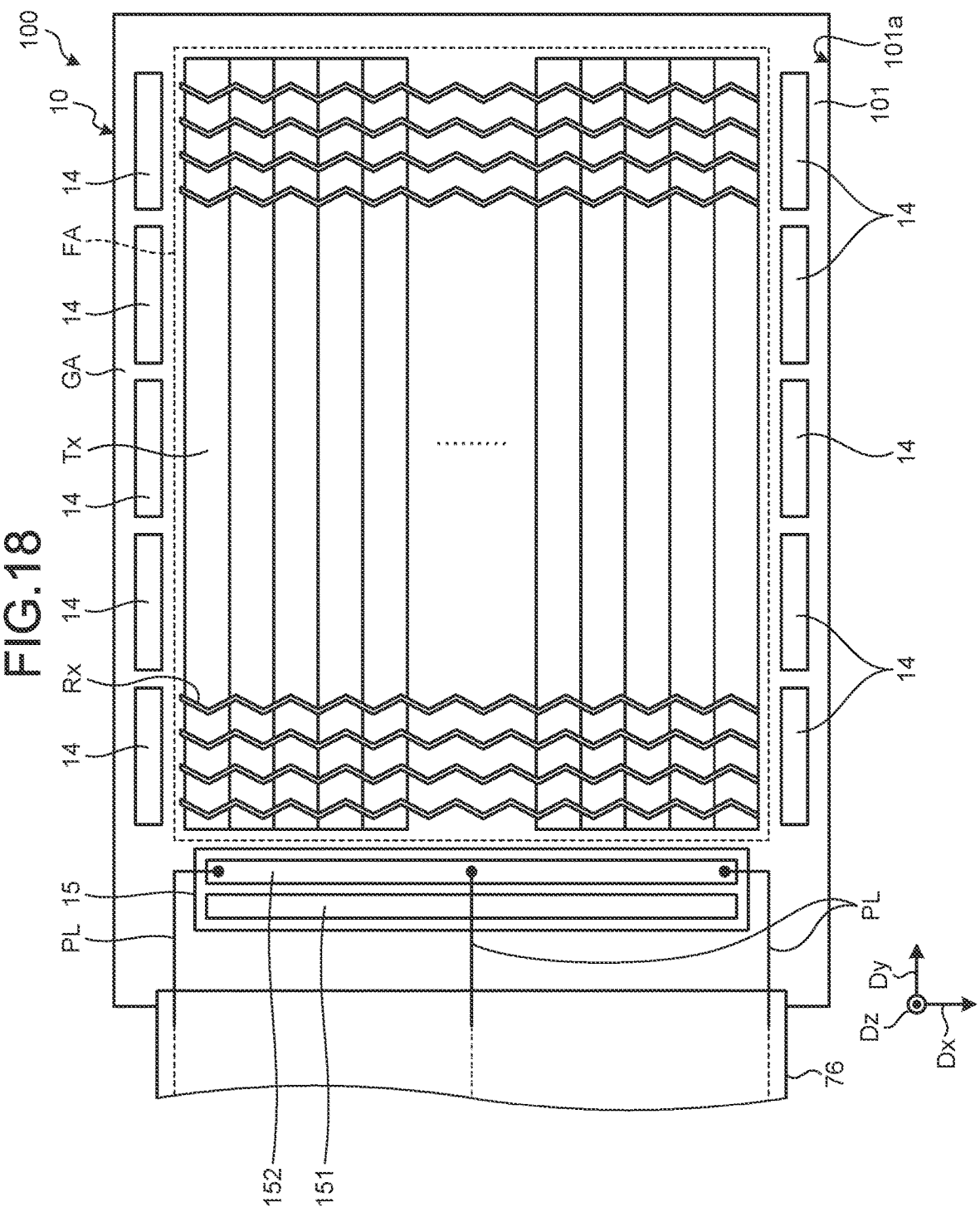
FIG. 18 is a plan view of the sensor according to a third embodiment.

FIG. 18 is a plan view of the sensor according to a third embodiment. In the third embodiment, the drive electrode driver 15 and the drive electrodes Tx are arranged in the second direction Dy, in which the drive electrodes Tx extend. A plurality of detection electrode selection circuits 14 are arranged so as to interpose the drive electrodes Tx therebetween in the first direction Dx. The drive electrodes Tx described above are arranged in the second direction Dy. The detection electrodes Rx are arranged in the first direction Dx orthogonal to the second direction Dy. Describing the first embodiment or the second embodiment with the first direction Dx and the second direction Dy exchanged can describe the third embodiment, and thus a detailed description of the sensor 10 is omitted.

The drive electrode driver 15 includes a shift register circuit 151 and a buffer circuit 152. The shift register circuit 151 successively selects the drive electrodes Tx in a time division manner. The buffer circuit 152 amplifies the drive signal Vs and supplies it to a selected drive electrode Tx. A plurality of power supply lines PL supply power to the buffer circuit 152 from the outside. The power supply lines PL supply power to both ends and a central part in the second direction Dy, for example. With this operation, without supplying power from the upper side, power can be directly supplied from the outside of the drive electrode driver 15, and a load during power supply is reduced.

Although the preferred embodiments and the modifications of the present invention have been described, the present invention is not limited to such embodiments and the modifications. The details disclosed in the embodiments and the modifications are only by way of example, and various modifications can be made without departing from the gist of the present invention. Although a transmissive liquid crystal display device enabling color display was shown as the display device 1 in the first embodiment, for example, the present invention is not limited to a color display-enabled transmissive liquid crystal display device and may be a monochrome display-enabled transmissive liquid crystal display device. Appropriate modifications made without departing from the gist of the present invention also naturally belong to the technical scope of the present invention.

The fingerprint detection device and the display device of the present aspect can take the following aspects, for example.

(1)

A fingerprint detection device including:

a substrate;

a plurality of drive electrodes provided on one face side of the substrate and arranged in a first direction; and a plurality of zigzag detection electrodes provided on the one face side and arranged in a second direction crossing the first direction, the detection electrodes having:

a plurality of first line parts;

a plurality of second line parts extending in a direction crossing the first line parts; and bent parts coupling the first line parts and the second line parts to each other, and the drive electrodes having:

a plurality of electrodes arranged spaced apart from each other in a plan view;

connecting parts coupling the electrodes adjacent to each other in the second direction to each other; and dummy electrodes in a floating state, each of the dummy electrodes being arranged between the two electrodes arranged in the first direction between the two detection electrodes.

(2)

The fingerprint detection device according to (1), in which the electrodes have a shape including two parallel sides, and sides of the dummy electrodes facing the electrodes are parallel to the sides of the electrodes.

(3)

The fingerprint detection device according to (1) or (2), in which a width given by extending a center line between a side of the electrode and a side of the dummy electrode facing the electrode along the side of the electrode and causing the center line to reach any of the electrodes, the dummy electrodes, and the connecting parts is larger than one time an arrangement spacing of the two bent parts in the second direction and smaller than three times the arrangement spacing.

(4)

The fingerprint detection device according to any one of (1) to (3), in which a center line between a side of the electrode and a side of the dummy electrode facing the electrodes is extended along the side of the electrodes, and an angle formed by the center line and the detection electrode is 90 degrees.

(5)

A fingerprint detection device including:

a substrate;

a plurality of drive electrodes provided on one face side of the substrate and arranged in a first direction; and a plurality of zigzag detection electrodes provided on the one face side and arranged in a second direction crossing the first direction, the detection electrodes having:

a plurality of first line parts;

a plurality of second line parts extending in a direction crossing the first line parts; and bent parts coupling the first line parts and the second line parts to each other, the drive electrodes having a plurality of electrodes having a shape including two parallel sides and arranged spaced apart from each other in a plan view, and a width given by extending a center line between sides of the electrodes facing each other along the sides of the electrodes and causing the center line to reach any of the electrodes and the connecting parts being larger than one time an arrangement spacing of the two bent parts in the second direction and smaller than three times the arrangement spacing.

(6)

The fingerprint detection device according to (5), in which an angle formed by the center line between the sides of the electrodes facing each other extended along the sides of the electrodes and the detection electrode is 90 degrees.

(7)

The fingerprint detection device according to any one of (1) to (6), in which the electrodes each include:

a first electrode; and a second electrode different in shape from the first electrode in a plan view.

(8)

The fingerprint detection device according to (7), in which a shape of the first electrode in a plan view is a parallelogram having two sides parallel to a direction in which the first line parts extend, and a shape of the second electrode in a plan view is a parallelogram having two sides parallel to a direction in which the second line parts extend and different in shape from the first electrode.

(9)

The fingerprint detection device according to any one of (1) to (8), in which the electrodes are translucent electrodes, and the detection electrodes are metallic thin lines.

(10)

The fingerprint detection device according to any one of (1) to (9), in which a ratio of an arrangement spacing of the bent parts to an arrangement spacing of the drive electrodes is 2 or less in the first direction.

(11)

The fingerprint detection device according to any one of (1) to (10), in which the connecting parts are alternately arranged on one side and another side of a virtual line passing through an areal gravity center of the electrodes in the second direction.

(12)

A display device including:

a display panel; and the fingerprint detection device according to any one of (1) to (11) arranged facing the display panel.

What is claimed is:

1. A fingerprint detection device comprising:

a substrate;

a plurality of drive electrodes provided on one face side of the substrate and arranged in a first direction; and a plurality of zigzag detection electrodes provided on the one face side and arranged in a second direction crossing the first direction, the detection electrodes having:

a plurality of first line parts;

a plurality of second line parts extending in a direction crossing the first line parts; and bent parts coupling the first line parts and the second line parts to each other, and the drive electrodes having:

a plurality of electrodes arranged spaced apart from each other in a plan view;

connecting parts coupling the electrodes adjacent to each other in the second direction to each other; and dummy electrodes in a floating state, each of the dummy electrodes being arranged between the two electrodes arranged in the first direction between the two detection electrodes.

2. The fingerprint detection device according to claim 1, wherein the electrodes have a shape including two parallel sides, and sides of the dummy electrodes facing the electrodes are parallel to the sides of the electrodes.

3. The fingerprint detection device according to claim 1, wherein a width given by extending a center line between a side of the electrode and a side of the dummy electrode facing the electrode along the side of the electrode and causing the center line to reach any of the electrodes, the dummy electrodes, and the connecting parts is larger than one time an arrangement spacing of the two bent parts in the second direction and smaller than three times the arrangement spacing.

4. The fingerprint detection device according to claim 1, wherein a center line between a side of the electrode and a side of the dummy electrode facing the electrode is extended along the side of the electrode, and an angle formed by the center line and the detection electrode is 90 degrees.

5. The fingerprint detection device according to claim 1, wherein the electrodes each include:

a first electrode; and a second electrode different in shape from the first electrode in a plan view.

6. The fingerprint detection device according to claim 5, wherein a shape of the first electrode in a plan view is a parallelogram having two sides parallel to a direction in which the first line parts extend, and a shape of the second electrode in a plan view is a parallelogram having two sides parallel to a direction in which the second line parts extend and different in shape from the first electrode.

7. The fingerprint detection device according to claim 1, wherein the electrodes are translucent electrodes, and the detection electrodes are metallic thin lines.

8. The fingerprint detection device according to claim 1, wherein a ratio of an arrangement spacing of the bent parts to an arrangement spacing of the drive electrodes is 2 or less in the first direction.

9. The fingerprint detection device according to claim 1, wherein the connecting parts are alternately arranged on one side and another side of a virtual line passing through an areal gravity center of the electrodes in the second direction.

10. A display device comprising:

a display panel; and the fingerprint detection device according to claim 1 arranged facing the display panel.

* * * * *